(12) United States Patent
Frome

(10) Patent No.: US 7,981,901 B2
(45) Date of Patent: *Jul. 19, 2011

(54) COMPOSITIONS AND METHODS FOR TARGETING CEREBRAL CIRCULATION AND TREATMENT OF HEADACHE

(76) Inventor: Bruce Frome, Beverly Hills, CA (US)

( * ) Notice: Subject to any disclaimer, the term of this patent is extended or adjusted under 35 U.S.C. 154(b) by 1503 days.

This patent is subject to a terminal disclaimer.

(21) Appl. No.: 10/483,509

(22) PCT Filed: Aug. 20, 2002

(86) PCT No.: PCT/US02/26613
§ 371 (c)(1),
(2), (4) Date: Jan. 12, 2004

(87) PCT Pub. No.: WO03/017932
PCT Pub. Date: Mar. 6, 2003

(65) Prior Publication Data
US 2004/0171625 A1    Sep. 2, 2004

Related U.S. Application Data

(63) Continuation-in-part of application No. PCT/US01/26459, filed on Aug. 23, 2001.

(51) Int. Cl.
*A01N 43/90* (2006.01)
*A01N 43/40* (2006.01)
*A61K 31/522* (2006.01)
*A61K 31/44* (2006.01)
*C07D 473/00* (2006.01)
*C07D 213/62* (2006.01)
*C07D 213/78* (2006.01)

(52) U.S. Cl. ............... 514/263.34; 514/335; 544/267; 546/298

(58) Field of Classification Search ............ 514/887, 514/929, 947, 927, 949
See application file for complete search history.

(56) References Cited

U.S. PATENT DOCUMENTS

| | | | | |
|---|---|---|---|---|
| 5,250,529 A | * | 10/1993 | Theoharides | 514/254.07 |
| 5,827,832 A | * | 10/1998 | Sandage et al. | 514/49 |
| 5,840,755 A | * | 11/1998 | Liedtke | 514/535 |
| 5,885,597 A | * | 3/1999 | Botknecht et al. | 424/401 |
| 5,897,880 A | * | 4/1999 | Drizen et al. | 424/488 |
| 6,582,724 B2 | * | 6/2003 | Hsu et al. | 424/449 |

OTHER PUBLICATIONS

O'Banion, M. K., "COX-2 and Alzheimer's disease: potential roles in inflammation and neurodegeneration", 1999, Exp. Opin. Invest. Drugs, 8(10), pp. 1523 and 1526.*

Mohiuddin, A.A.; Bath, F.J.; Bath, P.M., "Theophylline, aminophylline, caffeine and analogues for acute ischaemic stroke", 2000, Cochrane Database Systematic Reviews, 2, pp. 1 and 2.*

Darco et al., "Fever from caffeine", Mar. 1996, Allergy, vol. 51(3), abstract.*

Barth PMW, "Theophylline, aminophylline, caffeine and analogues for acute ischaemic stroke", Oct. 1996, Cochrane Database of Systematic Reviews, Issue 4, abstract.*

Winslow; E.H. "Digitalis", Jun. 1974, The American Journal of Nursing, vol. 74, No. 6, pp. 1062-1065.*

Brater, DC; "Benefits and risks of toraseamide in congestive heart failure and essential hypertension", Drug Safety, Feb. 1996, vol. 14, No. 2, abstract.*

* cited by examiner

*Primary Examiner* — Sreeni Padmanabhan
*Assistant Examiner* — Kendra D Carter
(74) *Attorney, Agent, or Firm* — Fish & Associates, PC

(57) ABSTRACT

Methods and compositions for targeting cerebral circulation and treatment of headache include formulations comprising a pharmacologically active substance in a transdermal formulation, which is topically applied to an area of skin superficial to a carotid artery, a temporal artery, a vertebral artery, or to a tender spot associated with a headache. Particularly preferred formulations include a xanthine derivative (e.g., theophylline, caffeine, aminophylline), and may further comprise ketoprofen. Contemplated methods further include methods of advertising use of contemplated compositions.

10 Claims, 1 Drawing Sheet

US 7,981,901 B2

COMPOSITIONS AND METHODS FOR TARGETING CEREBRAL CIRCULATION AND TREATMENT OF HEADACHE

This application is a continuation-in-part of, and claims the benefit to the PCT application with the serial number PCT/US01/26459, filed Aug. 23, 2001.

FIELD OF THE INVENTION

The field of the invention is compositions and methods for targeting cerebral circulation, and particularly relates to treatment of headache.

BACKGROUND OF THE INVENTION

Less severe to moderate headaches (e.g., tension headaches) are experienced by about seventy five percent of Americans, while more than forty percent of Americans experience six or more less severe to moderate headaches per year. Approximately twenty percent of people suffer at least one severe headache per year, and in North America alone 28 million people have been diagnosed with recurring migraines. Severe headaches often limit a person significantly in their ability to engage in life, and it is estimated that approximately 157 million working days per year are lost due to headaches.

It is generally believed that vascular headaches and particularly migraine are at least in part caused by swelling of blood vessels in the scalp, in the meninges (i.e., pia mater, dura mater, and arachnoid membrane), and/or in the brain itself. Both scalp and meninges are innervated by pain fibers, onto which the swollen vessels are thought to press. The swelling of the blood vessels can be triggered by a variety of factors, including intrinsic factors (e.g., stress), and/or extrinsic factors. For example, caffeine acts as a vasoconstrictive agent in the brain, and consequently many people experience headaches upon caffeine withdrawal.

There are various pharmacological treatments known in the art to reduce headaches. For example, many people use Aspirin™ (Acetylic salicylic acid) or Tylenol™ (Acetaminophen) to reduce their headache. Although such over-the-counter drugs are often relatively effective to at least reduce some of the pain, they tend to incur, and especially in higher dosages and/or prolonged administration, significant side effects (e.g., ulcers, increase in coagulation time, etc.).

In alternative treatments, pharmacologically active agents are systemically administered to target receptors that are functionally involved in vasoconstriction of blood vessels in the cerebral circulation, thereby relieving the pressure perceived as a headache. Examples for such pharmacologically active agents include triptans (e.g., Sumatriptan and Rizatriptan), and various ergots that target the 5HT receptors, which stimulate cerebral vasoconstriction [Hargreaves in *Cephalalgia* (2000) 20 Suppl 1:2-9].

In a still further example, caffeine and other methylxanthines (although vasodilating in the periphery) stimulate vasoconstriction in the cerebral circulation. Such methylxanthines are probably effective by stimulation of the release of endogenous epinephrine and norepinephrine, both of which are potent cerebral vasoconstrictors [Muller-Schweinitzer and Fanchamps in Adv. Neurol. (1982) 33:343-356]. Caffeine is a component of several over-the-counter migraine and headache medications. However, in known formulations caffeine needs to be orally ingested in substantial quantities to reduce a headache, which often produces undesirable side effects (e.g., excessive central nervous stimulation).

Although there are various methods and compositions known in the art to reduce headache and/or migraine, all or almost all of them suffer from one or more disadvantage. Therefore, there is still a need to provide improved methods and compositions for treatment of headache and/or migraine.

SUMMARY OF THE INVENTION

Methods and compositions are provided which are employed to target cerebral circulation and to treat headache. More particularly, contemplated methods and compositions include formulations comprising a pharmacologically active substance in a transdermal formulation, which is topically applied to an area of skin superficial to a carotid artery, a temporal artery, a vertebral artery, or to a tender spot associated with a headache.

In one aspect of the inventive subject matter, contemplated transdermal formulations comprise a skin penetration enhancer (e.g., an azone derivative, a synthetic terpene, oleic acid, N-methyl-2-pyrrolidone, an epsilon-aminocaproic acid ester, a lecithin organogel, a pluronic-lecithin-organogel, or an aromatic S,S-dimethyliminosulfurane). Particularly preferred pharmacologically active substances include xanthine derivatives (e.g., caffeine, theophylline, or aminophylline) in a concentration of at least 1% to 70%. Contemplated formulations may further include ketoprofen (2-(meta-benzoylphenyl)propionic acid) as a muscular-active substance in a concentration of about 0.5% (wt) to 50% (wt).

In another aspect of the inventive subject matter, a method of treating a person having a headache includes a step in which a tender spot associated with the headache on a body surface (particularly neck, face, and scalp) of the person is identified. In a further step, contemplated compositions are topically applied to the tender spot in an amount effective to reduce the headache.

In a further aspect of the inventive subject matter, a method of marketing a product includes one step in which contemplated compositions are included in the product. In a further step, a person is instructed to identify a tender spot associated with a headache on a body surface, and in a still further step, the person is instructed to topically apply the product to the tender spot in an amount effective to reduce the headache.

In yet another aspect, a method of marketing a product includes one step in which contemplated compositions (including skin penetration enhancer and pharmacological active substance) are included in the product, and in which a person is instructed to identify an area of skin superficial to a carotid artery, a temporal artery, or a vertebral artery. In a further step, the person is instructed to topically apply the product to the area in an amount effective to direct the pharmacological active substance to a cerebral circulation.

Various objects, features, aspects and advantages of the present invention will become more apparent from the following detailed description of preferred embodiments of the invention, along with the accompanying drawing.

DETAILED DESCRIPTION

Contemplated Compounds, Compositions, and Formulations

Figure 1:
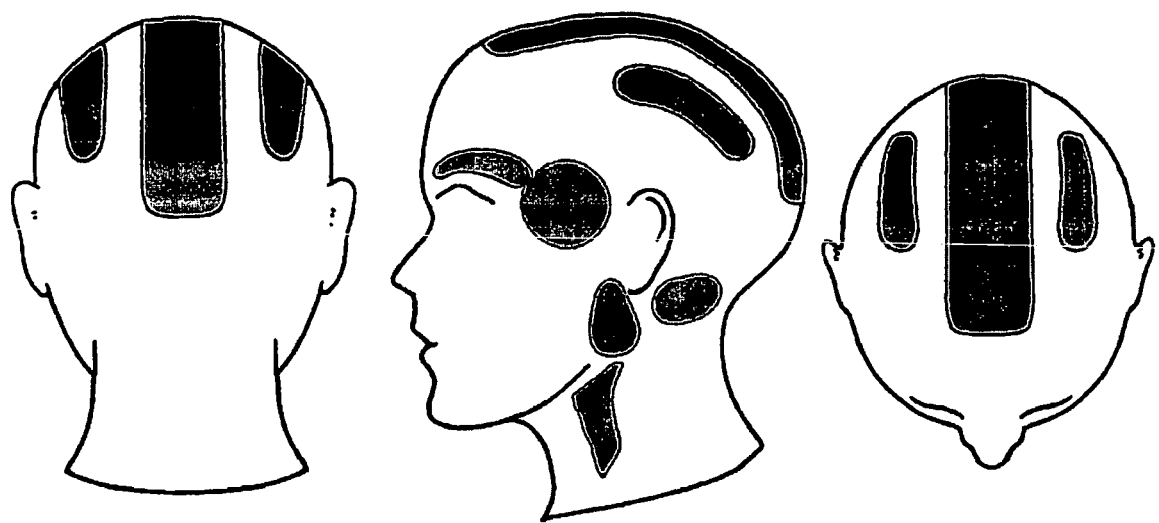
FIG. 1 is a schematic view of head and neck of a person depicting exemplary areas of application of contemplated compositions and formulations.

It is generally contemplated, that cerebral circulation can be targeted with various compositions comprising a pharmacologically active substance in a transdermal formulation, and that contemplated compounds (i.e., pharmacologically active substances), compositions, and formulations can advantageously be employed for treatment of various diseases or symptoms, particularly headache.

In a preferred aspect of the inventive subject matter, contemplated compositions include a pharmacologically active substance that preferably has a vaso-active effect. The term "vaso-active effect" as used herein includes vaso-constrictive (effecting at least 5% luminal constriction, more typically at least 10% luminal constriction) and vaso-dilatory effects (effecting at least 5% luminal dilation, more typically at least 10% luminal dilation). Consequently, particularly preferred pharmacologically active substances include xanthine derivatives according to structure 1, and especially include caffeine, theophylline, and dimeric forms such as aminophylline (ethylene diamine complex with theophylline).

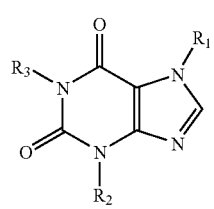

Structure 1 wherein $R_1$-$R_3$ are independently hydrogen, methyl, branched or unbranched lower alkyl, all of which may or may not further comprise functional groups (e.g., nucleophilic, electrophilic, polar, non-polar, etc.), and which may include one or more conjugated or nonconjugated π-bonds. Furthermore, one or more nitrogen atoms may be replaced with another heteroatom (e.g., O, S, Se, etc.), or be replaced with a carbon atom. Similarly, the carbonyl oxygen may be replaced with atoms other than oxygen, or substituted with a functional group (e.g., carboxylic acid, hydroxyl, nitrile, ethynyl, amino, imino, etc.).

In alternative aspects, suitable pharmacologically active compounds also include various vaso-active substances other than xanthine derivatives, and particularly include vitamin B6, digitalis, diuretics, or angiotensin-converting enzyme inhibitors. Where appropriate, it is also contemplated that nitrate-generating compounds (e.g., nitroglycerin, isosorbide-5-mononitrate, etc.) may be included in alternative compositions and formulations. In still further alternative aspects, vasodilators may be included to improve cerebral blood flow.

Where it is especially desirable that contemplated compositions include a muscular-active compound, it is contemplated that all known muscle relaxants are contemplated suitable for use herein. The term "muscular-active compound" as used herein refers to all compounds that modulate the tonus of a muscle. Particularly contemplated muscular-active compounds reduce the tonus of smooth muscles and/or voluntarily controlled muscles. For example, appropriate muscle relaxants include carisoprodol, cyclobenzaprine, chlorzoxazone, metaxolone, or methocarbamol. However, an especially preferred muscular-active compounds is ketoprofen (infra).

In yet further alternative aspects, it is contemplated that suitable compounds include all compounds that have a desired pharmacological activity in the cerebral circulation and/or the brain. For example, alternative drugs include drugs that interact with the hypothalamus, the hypophysis, receptors in the brain, or particular cells (e.g., neuronal cells, glial cells, astrocytes, etc.), which may or may not be diseased. Consequently, suitable compounds include fever reductants, anti-inflammatory drugs, anti-depressants, anti-coagulants, stimulants, cytokines, and so forth.

With respect to the amount of contemplated compounds, it should be appreciated that a particular amount of a particular pharmacologically active compound will typically depend on the desired strength of the formulation, the type of pharmacologically active compound, and the particular application of the formulation. Consequently, contemplated compounds may be in the range of less than 0.1% w/w to 90% w/w, and even more. More typically, contemplated compounds may be in the range of about 1% w/w to 20% w/w.

It is generally preferred that where the pharmacologically active substance is a xanthine derivative according to Structure 1, appropriate amounts will typically be within a range of 1% w/w to about 70% w/w, more preferably within the range of at least 2% w/w to about 50% w/w, and most preferably in the range of at least 4% w/w to about 15% w/w. Muscular-active compounds (e.g., Ketoprofen) are contemplated to be included in suitable formulations in a range of about at least 0.5% w/w to about 50% w/w, preferably at least 2% w/w to about 25% w/w, and more preferably between about at least 4% w/w to about 15% w/w.

In another preferred aspect of the inventive subject matter, contemplated compositions include a transdermal formulation (i.e., contemplated compounds are formulated in a transdermal formulation). The term "transdermal formulation" as used herein refers to any formulation that facilitates passage of a pharmacologically active substance across the epidermal layer into at least the papillary, and more preferably the reticular layer of the human dermis. There are numerous transdermal formulations known in the art, and all of the known transdermal formulations are considered suitable for use in conjunction with the teachings presented herein.

It is generally contemplated that suitable transdermal formulations include ionic compounds (e.g., ascorbate, calcium thioglycolate, cetyl trimethyl ammonium bromide, ionic surfactants, 5-methoxysalicylate, etc.), dimethyl sulfoxide and related compounds (e.g., cyclic sulfoxides, decylmethyl sulfoxide, etc.), azone and related compounds (e.g., 1-dodecyl azacycloheptan-2-one, N-Dodecyl-2-pyrrolidone, azacycloalkane derivatives, 1-geranylazacycloheptan-2-one, etc.). Further contemplated skin penetration enhancer include solvents (e.g., alkanols, esp. ethanol, dimethyl formamide, polyoxyethylene sorbitan monoesters, propylene glycol, etc.), or fatty alcohols, fatty acids, and related structures (e.g., aliphatic and lauryl alcohols, dodecyl N,N-dimethylamino acetate, ethyl acetate, alkanoic acids and oleic acids, isopropyl myristate, etc.). Still further contemplated formulations include enzymes (e.g., papain), amines and amides (e.g., N,N-Diethyl-m-toluamide), complexing agents (e.g., Brij, Pluronic, etc), and N-methyl pyrrolidone and related compounds (e.g., 1,3-Dimethyl-2-imidazolikinone or 2-Pyrrolidone).

Particularly suitable skin penetration enhancers include azone derivatives, natural and synthetic terpenoid compounds and their alcohols, oleic acid, N-methyl-2-pyrrolidone, epsilon-aminocaproic acid esters, lecithin organogels, pluronic-lecithin-organogels, aromatic S,S-dimethyliminosulfurane, Padimate O, oil-water emulsions with sub-micron droplets, capsaicin, and various esters of organic acids.

Contemplated compositions and formulations can be prepared using various protocols, and a particular composition will typically determine (at least in part) a particular protocol. There are numerous methods and protocols known in the art, and exemplary protocols and transdermal formulations are described in "Topical Drug Bioavailability, Bioequivalence, and Penetration" by Vinod P. Shah, Howard I. Maibach (Editor), Plenum Pub Corp; ISBN: 0306443678, or in "Percutaneous Penetration Enhancers" by Eric W. Smith (Editor), Howard I. Maibach (Editor), CRC Press; ISBN: 0849326052, or in "Pharmaceutical Skin Penetration Enhancement" by Kenneth A. Walters, Jonathan Hadgraft (Editor), Marcel Dekker; ISBN: 0824790170, or in "Drug Permeation Enhancement: Theory and Applications" by D. S. Hseih, Ed. (Dekker, New York, 1994), all of which are incorporated by reference herein.

Consequently, contemplated compositions and formulations are typically preparations for topical application, and particularly include preparations in form of a cream, gel, lotion, ointment, salve, or a paste. Alternatively, contemplated compositions and formulations may also include preparations in liquid form (e.g., a syrup, tincture, spray, drops, etc.), all of which may or may not be applied with a patch.

Especially preferred compositions include a xanthine derivative in a concentration of about 4% (wt) to 70% (wt) and ketoprofen in a concentration of about 0.5% (wt) to 50% (wt). With respect to the xanthine derivative, the same considerations as described above apply. Furthermore, such particularly preferred compositions may be formulated in a lecithin-containing formulation or a pluronic-lecithin-organogel formulation (supra). It should be especially recognized, that compositions including a xanthine derivative or an NSAID have generally been described in the art. However, the inventors observed that formulations including an NSAID other than Ketoprofen generally fail to provide relief in treatment of a headache, when topically applied to a person (either to a tender spot, or to an area superficial to a carotid artery, a temporal artery and/or a vertebral artery). It is therefore a surprising result that Ketoprofen is the only NSAID effective in treatment of a headache when used in protocols according to the inventive subject matter (see also examples). While not wishing to be bound by a particular hypothesis or theory, the inventors contemplate that the effect of Ketoprofen may be at least in part mediated by a muscle-relaxant effect rather than via a suppressive effect in inflammation.

It should further be appreciated that contemplated compounds (i.e., pharmacologically active substances) expressly exclude complex herbal extracts (i.e., herbal extracts prepared from more than one, more typically ore than five plants or plant parts) such as Tiger Balm, plant oils and essences.

Contemplated Uses

It is generally contemplated that compositions and formulations according to the inventive subject matter are topically applied onto the surface of a body of an animal, preferably a mammal, and most preferably a human. The term "surface of a body" as used herein refers to any surface on a body of a person that is directly and manually accessible by the same or other person, and particularly includes the scalp, neck, temples, and areas of skin superficial to a carotid artery, a temporal artery, and a vertebral artery. The term "superficial" as used herein means in a proximity of no more than 1 cm, preferably no more than 7 mm, and more preferably no more than 4 mm. It is further contemplated that such application will direct contemplated compounds to the cerebral circulation. While it is generally contemplated that all methods of topical application are considered suitable for use herein, particularly preferred methods include manual application (e.g., rubbing in or massaging in), application using a transdermal patch, and needle-less injection.

The term "cerebral circulation" as used herein refers to all blood vessels and compartments that supply blood and/or other physiological substances to and remove them from the cranial vault, and especially encompass the arterial systems of the head and neck, the venous system collecting and returning blood from the head to the trunk, the lymphatic systems draining the head and the cerebro-spinal fluid system bathing the brain, brain stem and spinal cord. Particularly contemplated blood vessels supply blood and physiological substances to the hypothalamus and are generally located above the trunk (i.e., areas including the neck and head).

In a preferred aspect of the inventive subject matter, approximately 200 mg to 1 g of contemplated compositions (e.g., 3.2% w/w theophylline and 2% w/w ketoprofen in a transdermal formulation in cream form) is applied in equal portions to the temples of a person and gently massaged into the skin using circular rubbing motions to lessen a headache. It is further preferred that the application is performed upon onset of the headache.

However, it should be appreciated that numerous alternative applications are also suitable and include alternative amounts, alternative compositions, alternative areas on the patient's body, and alternative methods of application. For example, where contemplated compositions and formulations include relatively large amounts of contemplated compounds, applications of less than 500 mg are suitable (e.g., between 50 mg and 500 mg, and even less). Similarly, where the application area is relatively large, or where the composition or formulation includes relatively small amounts of contemplated compounds, application of more than 1 g (e.g. 1 g to 5 g, and even more) are contemplated.

Similarly, the area of application need not be limited to an area superficial to a temporal artery (here: the temple), and numerous alternative areas are also considered suitable for application of contemplated compositions and formulations. For example, particularly preferred alternative areas include a skin area superficial to a carotid artery and a skin area superficial to a vertebral artery as depicted in FIG. 1 (shaded areas). Alternatively, contemplated compositions or formulations may be applied to any area of the body, so long as the application will result in directing contemplated compounds to the cerebral circulation.

Where manual application is less desirable, numerous applications methods other than manually rubbing are also contemplated and especially include application under occlusion (e.g., transdermal patch), electrophoretic application, needle-less injection, and spraying contemplated compositions and formulations onto the appropriate area. It should further be appreciated that the application may be performed by the patient, or be partially or entirely performed by another person.

Depending on the purpose of application (e.g., application to reduce fever, application to improve cerebral circulation, application to improve the mood of a patient), the composition of contemplated compositions and formulations may vary significantly. For example, where the pharmacological agent is an anti-depressant, application may be performed to improve the mood of the patient. On the other hand, where the pharmacological agent includes a fever reductant, application may be performed to normalize the body temperature of the patient. Moreover, where the pharmacological agent includes an anti-coagulant or vaso-dilator, application may be performed to reduce deleterious effects of impaired blood circulation (e.g., due to a stroke).

In another particularly preferred aspect of the inventive subject matter, contemplated compositions and formulations are employed to treat a headache, wherein a tender spot associated with the headache is identified on a body surface of a person. Contemplated compositions and formulations are then applied to the tender spot in an amount effective to lessen the headache. The term "tender spot" as used herein refers to a defined area on the body surface of a person that is (a) tender to the touch and (b) perceptible as tender only when the person suffers from a headache. Typically, a tender spot can be found by palpitation, and tender spots are often found on the parietal area (above the ears, forwards and behind), around the temples, or above the forehead. Tender spots are less frequently found on the top and rear of the skull. With respect to applications other than treatment of a headache, amounts administered to the patient, alternative compositions, areas on the patient's body, and methods of application, the same considerations as described above apply.

It should further be appreciated that contemplated compositions and formulations may be used for prophylactic, temporary, permanent, and acute treatment of the condition that is to be treated by administration of contemplated compositions and formulations.

Consequently, a method of directing a compound to a cerebral circulation comprises a step in which a composition having a pharmacologically active substance is provided, wherein the composition is formulated in a transdermal formulation. In a further step, the transdermal formulation is topically applied to an area of skin superficial to a carotid artery, a temporal artery, and/or a vertebral artery. Further contemplated methods include a method of treating a person having a headache, in which a composition having a pharmacologically active substance is provided. In a further step, a tender spot associated with the headache on a body surface of the person is identified, and in a still further step, the composition is topically applied to the tender spot in an amount effective to reduce the headache.

In further contemplated aspects of the inventive subject matter, and especially where contemplated compositions and formulations are produced and sold to the general public, it should be appreciated that a method of marketing a product may include a step in which a skin penetration enhancer is included as a component of the product. In a further step, a person is instructed to identify a tender spot associated with a headache on a body surface of the person, and in a still further step, the person is instructed to topically apply the product to the tender spot in an amount effective to reduce the headache.

Alternatively, a method of marketing a product may include a step in which a skin penetration enhancer and a pharmacological active substance are included as a component of the product. In a further step, the person is instructed to identify an area of skin superficial to at least one of a carotid artery, a temporal artery, and a vertebral artery, and in yet another step, the person is instructed to apply the product topically to the area in an amount effective to direct the pharmacological active substance to a cerebral circulation.

With respect to the skin penetration enhancer, the pharmacologically active substance, application method, amount, and area, the same considerations as described above apply. It is further preferred that the instruction comprises providing a printed information, and especially contemplated printed information includes written instructions, a pictogram, a graph, and/or a photographic image. Alternatively, numerous known alternative instruction methods (e.g., video class, internet class, person-to-person) are also considered suitable.

Cerebral Circulation and Directing a Compound to the Cerebral Circulation

It is known that pain sensed in the head during a headache originates in the optic division of the trigeminal nerve, which enervates the cerebral vasculature. Swelling of the intra and extra-cranial vasculature were first identified by Wolff and colleagues in the 1940's as key aspects of migraine [Wolff H. G.; Headaches and other head pain, 1st edition, Oxford University Press, London, 1948; and Meyer, Takashima, and Obara Headache Qtrly (1993) 4:222-235]. The pressure sensed by swelling of these vessels is thought to be transmitted through the trigeminal ganglion to the thalamus, and then to the cortex where the pain is experienced subjectively [Hargreaves in Cephalalgia (2000) 20 Suppl 1:2-9].

There are numerous triggers of migraine. However, migraine symptoms typically follow a uniform pattern, which are thought to originate in the hypothalmus upon integration of a variety of triggers by the cortex [Bruyn in *Adv. Neurol.* (1982) 33:151-169]. The concept of basilar arterial migraine, first presented by Bickerstaff [Lancet (1961) 1:15-17] unifies the vascular perfusion deficiency with the multitude of symptoms by proposing that the lower cerebral circulation at the level of the mid brain is the primary source of pathology. The thalamus and hypothalamus are the location of several regulatory nuclei of the sympathetic and parasympathetic regulatory centers, among them central regulation of blood pressure, sleep, water balance and body temperature.

Based on these observations, the inventors contemplated that a pharmacologically active agent for the treatment of headache must be delivered through the cerebral circulation to the area of the brain stem (e.g., hypothalamus or post ganglionic visceromotor and viscerosensory system of the pericarotid plexus) in order to act effectively. Conventionally, this is accomplished by oral delivery, injection, inhalation, or absorption through the rectal mucosa in a quantity sufficient to achieve an effective concentration in the blood plasma. Indeed, the entire body (especially the plasma) of a patient must be saturated with the agent in a conventional approach to achieve a therapeutic effect (and concentration of the pharmacologically active agent) in the brain. This process of saturating the plasma takes considerable time, except in the case of injection into a vein or inhalation, both of which are less preferable than oral administration.

The inventors have observed an unexpected result, in that topical application of a pharmacologically active agent to the skin superficial to the arteries of the extracranial circulation will direct (i.e., deliver) the agent to the cerebral circulation of the hypothalamus and midbrain, and that such a delivery requires significantly less agent to achieve a therapeutically effective concentration. In particular, the inventors contemplate that a pharmacologically active agent applied to the anterior triangle of the neck will penetrate the carotid sheath and enter the carotid blood supply of the brain and skull, or when applied below the ear behind the jawbone, the agent can enter the external carotid artery and its branches, or when applied to the temples, the agent will enter the superficial temporal artery and lacrimal arteries, as well as the maxillary and deep temporal arteries (Branching from the external carotid between the temple and below the ear, the middle meningeal and anterior tympanic arteries enter the posterior fossa, the chamber which contains the midbrain, through the jugular foramen and the condylar canal).

The inventors' observations and contemplations are supported by the fact that the circulation of the skull and scalp typically merge at their ends into other arteries. With respect to the scalp, Gray's Anatomy reads in pertinent parts " . . . their anastomoses are so free that as long as one is intact the detached scalp may be replaced with reasonable hope of its survival . . . " (35th Brit. ed. p. 629). Thus, the zygomatico-orbital artery arises from the superficial temporal artery, runs across the zygomatic arch to anastmose with the lacrimal and palpebral branches of the opthalmic artery from inside the skull. The parietal branch of the superficial temporal artery curves upwards and backwards on the side of the head and anastomoses with the opposite artery, as well as the posterior auricular and occipital arteries. These latter arteries penetrate passages at the rear and base of the skull, where they supply the tympanic chamber, glands, and probably anastomose with the meningeal artery. Therefore, the inventors contemplate that a substance entering the arteries below the temples can be distributed widely through the face and scalp, and through anastomoses enter the cerebral circulation of the skull.

Although the observations described herein and other experiments (data not shown) strongly suggest rapid delivery of effective concentrations of pharmacologically active agents to the midbrain, the inventors do not wish to be limited to the theory as outlined above. For example, it is contemplated that in alternative delivery routes the pharmacologically active agent reaches the hypothalamus through the diploic channel, after having been distributed somewhat by the arterial circulation. The venous drainage of the cerebral circulation passes through large sinuses before being gathered into the jugular vein and returned to the heart. In the sluggish flow of these sinuses, which pass directly behind and below the midbrain, the agent may diffuse out of the venous blood and enter the midbrain directly. Alternatively, or additionally, the agent may be entering the cerebrospinal fluid from the venous or arterial flow and reach the areas of action in this manner.

EXAMPLES

The following examples illustrate exemplary compositions, formulations, and methods of use according to the inventive subject matter.

Example 1

Exemplary Formulation with Aminophylline

One kilogram of lecithin with suitable purity (>95% acetone insoluble) (e.g., Spectrum brand (LE 102)) is combined with 600 ml octyl palmitate in a blender (e.g., Waring 1 liter stainless steel) until the mixture becomes a yellow, creamy fluid. Some lecithin granules may not be dissolved. The mixture is subsequently transferred to 500 ml beakers (350 ml±30 ml per beaker). A magnetic stirrer bar is added to each beaker and the mixtures are stirred for at least 12 hours. The resulting stirred solution has a dark amber color, and is translucent with a syrupy consistency.

The pharmacologically active substance (here: aminophylline) is dissolved in, or added to purified water, preferably in half the anticipated amount of purified water (here: in 50 ml) for the entire preparation. The aqueous solution comprising the pharmacologically active substance is slowly added to the lecithin syrup (e.g., by hand-stirring or small hand blender). The lecithin syrup will start to gel as soon as the aqueous solution is added.

Following the addition of the active solution, continue to add water one ml at a time (here:50 ml) while mixing. Thus, the exemplary formulation (4% w/w with respect to pharmacologically active substance) comprises 1,000 gram lecithin, 510 gram octyl palmitate, 100 gram water, and 64.4 gram of aminophylline.

Example 2

Exemplary Formulation with Penetration Enhancer

The oil phase of this composition comprises 100 g (here: 10%, typically between 5-15%) granular lecithin of suitable purity (>95% acetone insoluble, with >92% phosphatidylcholine content) and 100 g (here: 10%, typically between 5-15%) isopropylmyristate. The water phase comprises 200 g (here:20%) Polyoxamer F127 (Dow Corning) (Pluronic), 100 mg sorbic acid, and 600 ml (here:60%) purified water. The active ingredient (here: e.g., 3.2% (w/w) theophylline) is dissolved in the appropriate phase (i.e., water soluble active ingredients in the water phase, and lipid soluble active ingredients in the lipid phase). The final formulation is then prepared by adding the water phase to the oil phase, and blending the two phases to completion. The pH was adjusted to less than 7.0, most typically to about 5.3-5.6 using acid or base.

Example 3

Exemplary Formulation with Ketoprofen

Same as in Example 2, comprising 3.2% (w/w) theophylline and 2% (w/w) Ketoprofen as active ingredients.

Example 4

Exemplary Formulation with Penetration Enhancer and Acetaminophen

Same as in Example 2, comprising 5% (w/w) acetaminophen as active ingredient.

Example 5

Delivery of Acetaminophen to the Thalamic and Hypothalamic Region

Acetaminophen is usually indicated for fever reduction and is thought to modulate the body temperature through interaction with thermoregulatory nuclei in the hypothalamus. Acetaminophen is typically given as drops in children running a high fever at a dosage of about 160 mg for a child of 2-3 years in age. Using oral delivery, acetaminophen will enter the blood stream through the stomach, and will require approximately at least 20 minutes to achieve sufficient concentration in the plasma to lower the fever.

To demonstrate delivery of pharmacologically active agents to the cerebral circulation (here: the thalamic and hypothalamic region), a skin-penetrating formulation of acetaminophen as described in Example 4 was applied in a single dosage of 25 mg acetaminophen (corresponding to 500 mg of the formulation) to the temples of a group of patients with a fever of between about 38.5° C. to about 39.5° C. In this group, the fever was reduced within three minutes in all of the twenty children and adults within the group. If transdermal delivery would have occurred systemically, insufficient quantities of acetaminophen would have been administered for significant fever reduction since the total dosage applied to the skin was less than 25 mg (and the amount penetrating the skin likely to be less than 15 mg). Moreover, significant fever reduction was achieved in about 10% of the time required for oral administration. Therefore, and for reasons contemplated above, the inventors conclude that acetaminophen entered the cerebral circulation and reached the temperature-regulating center in the hypothalamus via the temporal artery by topically applying a transdermal formulation containing acetaminophen. Of course, it should be recognized that numerous other fever reducing agents may also be employed in contemplated formulations. For example, it is contemplated that all known non-steroid anti-inflammatory agents may be included (alone or in combination with other fever reducing agents), and a particularly preferred non-steroid anti-inflammatory agent is acetaminophen or aspirin.

Consequently, the inventors contemplate that an essential aspect of directing a pharmacologically active agent to the cerebral circulation includes formulation of the agent in a skin penetration-enhancing vehicle (transdermal formulation). In formulations without penetration enhancers, only a fraction of a pharmacologically active agent applied to the skin will penetrate percutaneously. The amount that penetrates is typically limited by the amount applied, the way the material is spread out on the skin, and the speed with which the vehicle dries. Once the vehicle is dry, the agent will precipitate and no further material can enter the skin through the outer layer, the stratum corneum. Conventional vehicles can deliver no more than micrograms of agent through the stratum corneum under normal circumstances [Flynn; "Topical and transdermal delivery—provinces of realism." in Dermal and Transdermal Drug Delivery edition, CRC Press, Inc., Boca Raton, Florida, 1993, ISBN: 3804712231].

Alternative particularly suitable skin penetration enhancers include azone derivatives, synthetic and natural terpenes, oleic acid, N-methyl-2-pyrrolidone, epsilon-aminocaproic acid esters, lecithin organogels, pluronic-lecithin-organogels, aromatic S,S-dimethyliminosulfuranes, Padimate O, oil-water emulsions with sub-micron droplets, and capsaicin. Similarly, alternative xanthine derivatives include caffeine, theophylline, and aminophylline, in concentrations preferably of at least 2% wt, more preferably at least 4% wt. Additionally, suitable formulations may further include muscle-active substances, and particularly Ketoprofen (preferably in a concentration of at least 0.5% wt to at least 10% wt). With respect to still further alternative compounds, compositions, and formulations, the same considerations as described above apply.

Example 6

Treatment of Acute Headache

The formulation of Example 1 was tested in a prospective clinical trial at the Pain Centers of America (415 North Crescent Drive Beverly Hills 90210, Calif). 155 patients were screened for headache history and other eligibility criteria, and 106 patients gave informed consent and entered the trial. The temples were prepared by cleaning using witch hazel and alcohol astringent. One milliliter of the formulation was applied to each temple and rubbed into the skin until it was absorbed completely. Headache relief was rapid, within 5 minutes of application for 81 patients. Evaluation was determined by achieving a score of 7 out of 10 on a VAS pain relief scale. Eleven of these patients had a return of their pain by 15 minutes. These patients reapplied the gel and eight out of the eleven had relief persisting at least one hour from the second application. Consequently, the formulation was effective for 78 out of 106 patients (74%). Interestingly, non-responders to the gel were heavy users of analgesics, especially opioids. Consequently, it is contemplated that success rates among the general population may well be higher than 74% of patients in this trial.

Example 6A

Treatment of Postdural Puncture Headache

The formulation of Example 1 (with 10% aminophylline) was tested in a prospective clinical trial at the Pain Centers of America (415 North Crescent Drive Beverly Hills 90210, Calif). 24 patients were screened for headache history and other eligibility criteria, and 21 patients gave informed consent and entered the trial.

The temples were prepared by cleaning using witch hazel and alcohol astringent. One milliliter of the formulation was applied to each temple and rubbed into the skin until it was absorbed completely. Headache relief was rapid, within about 10 minutes of application for 18 patients. Evaluation was determined by achieving a score of 7 out of 10 on a VAS pain relief scale. Where pain symptoms reappeared (three patients), the patients reapplied the gel and two of the three had relief persisting at least one hour from the second application.

Example 7

Prophylactic Treatment of Headache

For evaluation of prophylactic treatment of headache, formulation and application similar to the protocol as described in Example 6 was used. Patients with a history of recurring headaches were sent home with a supply to test prophylactic efficacy and safety. The patients applied the gel to the temples before meals (3× daily). 62% did not experience a severe headache in the 30-day test period. The remaining subjects who had a headache despite the use of the gel were asked to try an additional dosage at bedtime during the second month of observation. An additional 11% found this an effective prophylaxis, yielding total headache prevention for 73% of patients. Furthermore, non-responders to prophylactic treatments still found immediate relief at the beginning of the headache using the medication. In the end, 86% of the responding patients in the study reported that the gel was the most effective abortive headache treatment they had ever used. It should further be appreciated that contemplated prophylactic treatments will also be effective to prevent onset and/or lessen the severity of morning sickness and fibromyalgia, and especially preferred xanthine derivatives for these symptoms include aminophylline).

Example 8

Treatment of Acute Headache Using Tender Spot

The formulation of Example 1 was tested in a prospective study including 120 patients suffering from intermittent acute headaches. A first group of patients was instructed to locate a tender spot on their scalp and to topically apply about 500 mg of the formulation to the tender spot, while a second group was instructed to apply about 500 mg of the formulation to the pulse points of their temples under a protocol similar as described in example 6. Application to the pulse points lead to rapid relief of the headache within 2-5 minutes in about 75% of the patients, while application to the tender spot lead to almost instantaneous relief in almost all of the patients.

While not wishing to be bound by a particular theory, it is contemplated that the tender spot corresponds to the location where arteries branching from the external carotid artery enter the skull and anastomose with arteries of the cerebral circulation. Swelling of the scalp arteries (as a result of the headache) constricts the vessels at their passage through the skull bone, which is experienced as local pain, inflammation or tenderness.

Particularly contemplated alternative formulations include skin penetration enhancers such as azone derivatives, synthetic terpenes, oleic acid, N-methyl-2-pyrrolidone, epsilon-aminocaproic acid esters, pluronic-lecithin-organogels, or aromatic S,S-dimethyliminosulfurane. Especially contemplated pharmacologically active substances comprise a vasoactive substance such as xanthine derivatives, and may further comprise a muscular-active substance (e.g., Ketoprofen). With respect to still further alternative compounds, compositions, and formulations, the same considerations as described above apply.

Example 9

Treatment of Acute Headache Using Tender Spot and Ketoprofen

The formulation of Example 3 (comprising 3.2% (w/w) theophylline and 5% ketoprofen as active ingredients) was tested in a group of 25 patients suffering from cervicogenic headache. The patients were instructed to rub approximately 1 ml of the formulation onto the back of their neck, and to reapply the formulation when needed. Where treatment of headaches was performed using a protocol according to any one of examples 5-9, reduction in pain was observed in at least 60%, more typically in at least 70%, and most typically in at least 85% of all patient. The subjective pain relief was generally at least 4, more typically at least 5, and most typically at least 7 on a 10-point scale (VAS pain relief scale).

Example 10

Treatment of Transient or Non-Transient Stroke

Ischemic stroke is a temporary (e.g., transient) or permanent medical condition characterized at least in part by the lack of oxygen supply to the brain, which may lead to reversible or irreversible paralysis and/or cell death. Death or damage to a group of nerve cells in the brain is often due to interrupted blood flow, caused by a blood clot or blood vessel bursting. Depending on the area of the brain that is damaged, a stroke can cause coma, paralysis, speech problems and dementia. Stroke may be treated by bolus injection of niacin, which is thought to dilate the arteries and permits blood flow to resume.

The inventor now discovered that stroke can be treated using compositions according to the inventive subject matter. Two patients were treated for stroke, with the following results. Patient A was brought to the inventor by a relative. He demonstrated typical symptoms of aphasia, drooping of the right side of the face, and disorientation. A skin-penetrating formulation of niacin as described in Example 1 (see above, active ingredient 5% (w/w) niacin) was applied in a single dosage of 50 mg niacin (corresponding to 1 gram of formulation) to the anterior triangle of the neck on the side exhibiting paralysis. The formulation was gently massaged into the skin overlying the common carotid artery. The patient awoke from the disorientation within minutes, having regained control of speech and without paralysis.

Patient B was treated at home, after his wife summoned the inventor. The patient was immobile in a bed, due to partial paralysis and was speaking nonsense syllables. He was in a state of distress, but unable to communicate. A skin-penetrating formulation of niacin as described above was applied in a single dosage of 50 mg niacin (corresponding to 1 gram of formulation) to the anterior triangle of the neck on the side exhibiting paralysis. Within minutes the patient returned to a normal state of consciousness and was able to communicate. In both of these patients there were no remaining symptoms of stroke, due to the speed of recovery.

Consequently, the inventors contemplate methods of treatment of a patient having an ischemic stroke, in which a composition including a vasodilatory agent and/or an anticoagulant is provided. The composition is included in a transdermal formulation, and the transdermal formulation is topically applied to at least one area of skin superficial to a carotid artery, a temporal artery, and a vertebral artery in an amount effective to deliver the vasodilatory agent and/or anticoagulant to the cerebral circulation, thereby improving blood flow in an area affected by reduction of blood flow.

With respect to suitable vasodilatory agents it is contemplated that all known vasodilators are considered appropriate. However, particularly preferred vasodilatory agents include niacin, nitroglycerin, various nitrates, and hydralazine. Still further it should be appreciated that contemplated formulations may further include an anti-pyretic compound as previous studies have indicated beneficial effects of hypothermal treatment in incomplete cerebral ischemia (see e.g., Hoffman et al. in J. Neurosurg. Anesthesiol. 1991; 3:34-38). Alternatively, antipyretics may also be coadministered using non-transdermal routes. It is generally contemplated that all known anti-pyretics are suitable for use herein, however, especially contemplated anti-pyretics include acetaminophen, dipyrone, and aspirin.

Thus, specific embodiments and applications of compositions and methods for targeting cerebral circulation and treatment of headache have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A method of directing a topically applied pharmacologically active substance to a cerebral circulation, comprising:
   providing a composition that includes a pharmacologically active substance selected from the group consisting of xanthine derivative, vitamin B6 and angiotensin-converting enzyme inhibitors;
   including the composition in a transdermal formulation other than a patch; and
   topically applying the transdermal formulation to a tender spot associated with the headache or at least one area of skin superficial to a temporal artery and a vertebral artery, wherein the pharmacologically active substance is applied in an amount of less than 5 mg per dose to the cerebral circulation.

2. The method of claim 1 wherein the composition comprises a skin penetration enhancer selected from the group consisting of an azone derivative, a synthetic terpene, oleic acid, N-methyl-2-pyrrolidone, an epsilon-aminocaproic acid ester, a lecithin organogel, a pluronic-lecithin-organogel, and an aromatic S,S-dimethyliminosulfurane.

3. The method of claim 1 wherein the composition comprises a skin penetration enhancer selected from the group consisting of natural terpenes, Padimate O, oil-water emulsions with sub-micron droplets, and capsaicin.

4. The method of claim 1 wherein the pharmacologically active substance comprises a xanthine derivative.

5. The method of claim 4 wherein the xanthine derivative comprises caffeine.

6. The method of claim 4 wherein the xanthine derivative comprises theophylline.

7. The method of claim 4 wherein the xanthine derivative comprises aminophylline.

8. The method of claim 4 wherein the xanthine derivative has a concentration of at least 2% (wt).

9. The method of claim 4 wherein the xanthine derivative has a concentration of at least 4% (wt).

10. The method of claim 1 wherein the step of topically applying is undertaken to lessen a headache.

* * * * *